United States Patent [19]
Arlt

[11] Patent Number: 4,628,118
[45] Date of Patent: Dec. 9, 1986

[54] 5,5-DICHLORO-3,3-DIMETHYLPENTANOIC ACID

[75] Inventor: Dieter Arlt, Cologne, Fed. Rep. of Germany

[73] Assignee: Bayer Aktiengesellschaft, Leverkusen, Fed. Rep. of Germany

[21] Appl. No.: 786,251

[22] Filed: Oct. 10, 1985

Related U.S. Application Data

[62] Division of Ser. No. 518,855, Aug. 1, 1983, abandoned.

[30] Foreign Application Priority Data

Aug. 14, 1982 [DE] Fed. Rep. of Germany ....... 3230274

[51] Int. Cl.$^4$ .................. C07C 53/19; C07C 59/147; C07D 309/30; C07D 309/32
[52] U.S. Cl. .................................. 562/602; 549/292; 549/294; 562/577
[58] Field of Search ........................... 562/602

[56] References Cited

U.S. PATENT DOCUMENTS 3,155,685 11/1964 Prill et al. ............................ 549/292
4,235,780 11/1980 Kondo et al. ....................... 549/294
4,348,535 9/1982 Schmidt ............................. 549/292

FOREIGN PATENT DOCUMENTS 0031932 7/1981 European Pat. Off. .
3045555 7/1982 Fed. Rep. of Germany ...... 549/294

OTHER PUBLICATIONS

Houben-Weyl, Methoden der Organischen Chemie, vol. VI/2 (1963), pp. 580, 588.
J. Bredt, Justus Liebig's Annalen der Chemie, vol. 256 (1890), pp. 314–327.
Chemical Abstracts, vol. 68, Formula Index, p. 199F.
Chemical Abstracts, vol. 68, 1968, 5708.

Primary Examiner—Natalie Trousof
Assistant Examiner—Patricia M. Scott
Attorney, Agent, or Firm—Sprung, Horn, Kramer & Woods

[57] ABSTRACT

The following process steps are shown:

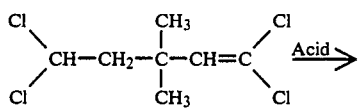

(V)

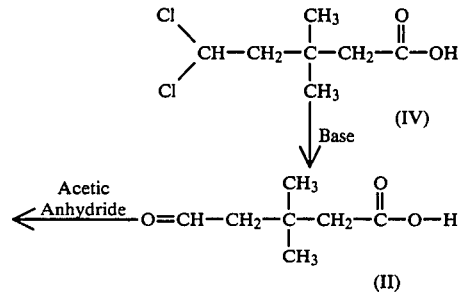

(IV)

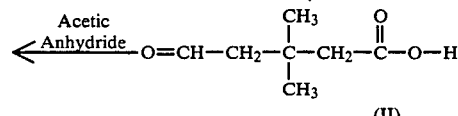

(II)

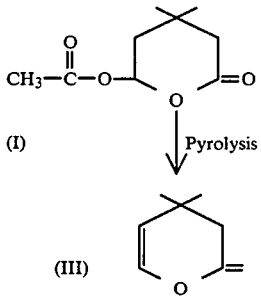

(I)

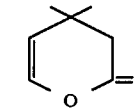

(III)

Intermediates I, II and IV are new. End product III is known, useful as an intermediate in the manufacture of pesticides, pharmaceuticals and dyestuffs.

1 Claim, No Drawings

5,5-DICHLORO-3,3-DIMETHYLPENTANOIC ACID

This is a division of application Ser. No. 518,855 filed Aug. 1, 1983, abandoned.

The present invention relates to 4,4-dimethyl-6-acetoxy-valerolactone, a process for its preparation and new intermediate products for this purpose, as well as its use for the preparation of 4,4-dimethyl-3,4-dihydro-α-pyrone.

It has been disclosed that 4,4-dimethyl-3,4-dihydro-α-pyrone can be obtained by the reaction route represented below (see EP-OS [European Published Specification] 31,932):

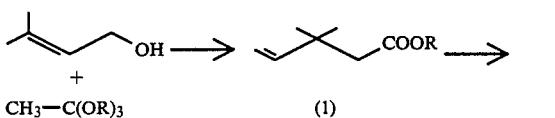

(1)

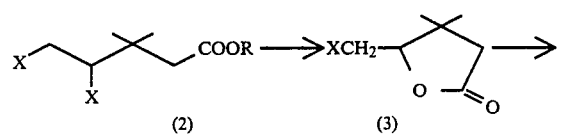

(2)  (3)

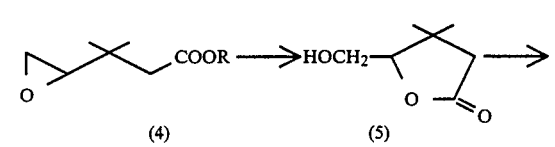

(4)  (5)

(6)

The following have been found:
1. 4,4-Dimethyl-6-acetoxy-valerolactone of the formula I

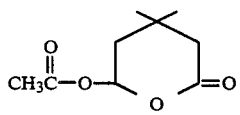   I

2. A process for the preparation of 4,4-dimethyl-6-acetoxy-valerolactone of the formula I

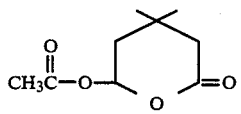   I which is characterized in that 3,3-dimethyl-5-oxo-pentanoic acid of the formula II

   II is reacted with acetic anhydride.

3. Use of 4,4-dimethyl-6-acetoxy-valerolactone of the formula I according to (1) above for the preparation of 4,4-dimethyl-3,4-dihydro-α-pyrone of the formula III

   III characterized in that 4,4-dimethyl-6-acetoxy-valerolactone of the formula I is pyrolyzed.

4. 3,3-Dimethyl-5-oxo-pentanoic acid of the formula II

   II

5. Process for the preparation of 3,3-dimethyl-5-oxo-pentanoic acid of the formula II according to (4) above, characterized in that 5,5-dichloro-3,3-dimethylpentanoic acid of the formula IV

   IV is reacted with bases.

6. 5,5-Dichloro-3,3-dimethylpentanoic acid of the formula IV

   IV

7. Process for the preparation of 5,5-dichloro-3,3-dimethylpentanoic acid of the formula IV according to (6) above, characterized in that 1,1,5,5-tetrachloro-3,3-dimethyl-pentene of the formula V

   V is subjected to acid hydrolysis.

With the aid of the new 4,4-dimethyl-6-acetoxy-valero-lactone of the formula I, 4,4-dimethyl-3,4-dihydropyrone can be produced economically on a large scale.

4,4-Dimethyl-6-acetoxy-valerolactone of the formula I is prepared by reacting 3,3-dimethyl-5-oxo-pentanoic acid with acetic anhydride. The reaction is carried out in the liquid phase, the mixture being warmed to approximately 80°–140° C., preferably 100°–140° C., preferably 120°–140° C. Preferably, catalysts such as, for example, $ZnCl_2$, $FeCl_3$ or $BF_3$, are added to the reaction mixture to effect a more rapid reaction. At least equivalent amounts of acetic anhydride are employed, but an excess does not have an adverse effect.

The reaction mixture can be worked up by fractional distillation to isolate and purify 4,4-dimethyl-6-acetoxy-valerolactone. However, the reaction mixture can also be processed further, without being worked up, to give 4,4-dimethyl-3,4-dihydro-α-pyrone of the formula III.

The preparation of 4,4-dimethyl-3,4-dihydro-α-pyrone of the formula III from 4,4-dimethyl-6-acetoxy-valerolactone of the formula I by splitting off acetic acid is carried out in the gas phase at elevated temperatures. For example, the compound of the formula I, in liquid form, is metered into a heated tube, vaporization and reaction taking place. The reaction gases are then cooled and condensed. The pyrolysis is carried out under atmospheric pressure or reduced pressure. The pyrolysis tube can be employed with or without packing materials. The packing material essentially serves to transfer heat. For example, packing materials composed of quartz, glass, porcelain, aluminum oxide, clay or iron are suitable for this purpose. The pyrolysis temperatures which are advantageously employed are between 300° and 500° C., preferably between 350° and 450° C.

In an advantageous embodiment of the process according to the invention, the preparation and cleavage of the 4,4-dimethyl-6-acetoxy-valerolactone by a procedure in which 3,3-dimethyl-5-oxo-pentanoic acid of the formula II is used as a starting material are combined in one process stage.

In this case, 3,3-dimethyl-5-oxo-pentanoic acid is reacted with acetic anhydride, if appropriate with the addition of the stated catalysts, in the gas phase, at temperatures between 300° and 500° C.

The mixture of substances obtained after the gas-phase reaction is separated by fractional vacuum distillation.

3,3-Dimethyl-5-oxo-pentanoic acid of the formula II is new. It can be prepared by reacting 5,5-dichloro-3,3-dimethylpentanoic acid of the formula IV with bases.

Examples of suitable bases are alkali metal hydroxides or alkaline earth metal hydroxides, tertiary amines, and alkali metal carbonates or alkaline earth metal carbonates.

Water is preferably used as a solvent. However, the reaction can also be carried out in water-containing water-immiscible solvents, such as aliphatic or aromatic hydrocarbons or ethers, such as tetrahydrofuran. Customary phase-transfer catalysts, such as tetraalkylammonium hydroxides, can be added as catalysts. The reaction is carried out at temperatures of 80°–120° C., preferably above 90° C.

The reaction is carried out under atmospheric pressure or slightly elevated pressure. The base is employed in an equimolar amount, or if appropriate in an excess of up to 10%.

5,5-Dichloro-3,3-dimethylpentanoic acid need not be employed in pure form; it can also be employed in the form of the reaction mixture obtained when it has formed.

5,5-Dichloro-3,3-dimethyl-pentanoic acid is new. It can be obtained by acid hydrolysis of 1,1,5,5-tetrachloro-3,3-dimethyl-pentene of the formula IV.

The hydrolysis is carried out in a temperature range of about 20°–100° C., preferably of 40°–70° C. In general, an excess of acid is employed, but the reaction mixture should at least contain an amount of water equivalent to the product of the formula V employed. In addition to sulphuric acid, other strong acids, such as, for example, phosphoric acid, methanesulphonic acid, trifluoroacetic acid and mixtures of formic acid and hydrochloric acid, are also suitable for the hydrolysis.

If it is desired to isolate the acid of the formula IV, the reaction mixture is diluted with water, and the acid (IV) is extracted with solvents, such as, for example, chlorohydrocarbons. When distillable acid mixtures, such as, for example, the reaction mixtures obtained after the hydrolysis with trifluoroacetic acid or formic acid/hydrochloric acid, are used, the mixture is worked up by distillation in order to obtain the acid (IV) in pure form.

1,1,5,5-Tetrachloro-3,3-dimethyl-pentene is known, and is obtained in very good yields at the present time from carbon tetrachloride, iso-butene and vinyl chloride.

EXAMPLE 1

5,5-Dichloro-3,3-dimethyl-pentanoic acid 500 g of 1,1,5,5-tetrachloro-3,3-dimethyl-pentene are metered into 2400 ml sulphuric acid (96%) while stirring, in the course of 1 hour at a rate such that the reaction mixture does not exceed 45° C. The reaction mixture is kept at 40°–45° C. for a further 24 hours, and is then introduced onto 3 kg of ice. The mixture is extracted several times with dichloromethane. After the solvent has been distilled off, 420 g of crude 5,5-dichloro-3,3-dimethyl-pentanoic acid are obtained, and after distillation 380 g of pure 5,5-dichloro-3,3-dimethyl-pentanoic acid of boiling point 103°–106° C./0.2 are obtained.

EXAMPLE 2

3,3-Dimethyl-5-oxo-pentanoic acid 30 g of 5,5-dichloro-3,3-dimethylpentanoic acid and 18 g of NaOH, dissolved in 20 ml of water, are metered simultaneously into 60 ml of water while the pH is monitored, the metering being carried out at a rate such that the pH is 9–10 during the reaction. As soon as the pH value remains constant, the reaction is complete. The reaction mixture is brought to pH 3 with hydrochloric acid, and is extracted with dichloromethane. 20.9 g of 4-chloro-3,3-dimethyl-5-oxo-pentanoic acid of boiling point 110°–115° C./0.09 are obtained.

EXAMPLE 3

4,4-Dimethyl-6-acetoxy-valerolactone 127 g of crude 3,3-dimethyl-5-oxo-pentanoic acid obtained according to Example 2 are warmed with 400 g of acetic anhydride at 120° C.–140° C. for 5 hours, 0.5 g of ZnCl$_2$ being added. The reaction mixture is fractionally distilled. 145 g of pure 4,4-dimethyl-6-acetoxy-valerolactone of boiling point 102°–105° C./0.2 are obtained.

EXAMPLE 4

4,4-Dimethyl-3,4-dihydro-α-pyrone 217 g of 4,4-dimethyl-6-acetoxy-valerolactone are metered uniformly into a pyrolysis tube (diameter 19 mm, length 20 cm) in the course of 6 hours, under a protective gas (N$_2$). The pyrolysis temperature, which is established by heating electrically, is 380° C. The pyrolysis product is fractionally distilled. 118 g of 4,4-dimethyl-3,4-dihydro-α-pyrone (b.p. 64°–66° C./10) are obtained, in addition to 24 g of starting material.

It will be appreciated that the instant specifiction and examples are set forth by way of illustration and not limitation, and that various modifications and changes may be made without departing from the spirit and scope of the present invention.

I claim:

1. 5,5-Dichloro-3,3-dimethylpentanoic acid of the formula

* * * * *